US006991605B2

(12) United States Patent
Lim

(10) Patent No.: US 6,991,605 B2
(45) Date of Patent: Jan. 31, 2006

(54) THREE-DIMENSIONAL PICTOGRAMS FOR USE WITH MEDICAL IMAGES

(75) Inventor: Richard Y. Lim, Issaquah, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 454 days.

(21) Appl. No.: 10/325,557

(22) Filed: Dec. 18, 2002

(65) Prior Publication Data
US 2004/0122310 A1   Jun. 24, 2004

(51) Int. Cl.
A61B 8/00 (2006.01)

(52) U.S. Cl. ..................... 600/443; 128/916
(58) Field of Classification Search ........ 600/407–471; 128/916; 345/419, 619–621, 630, 649–650, 345/653, 664, 679, 835–836; 382/128
See application file for complete search history.

(56) References Cited

U.S. PATENT DOCUMENTS

| 4,287,504 A | * | 9/1981 | Simon et al. ............... 340/462 |
| 5,211,167 A | * | 5/1993 | Amenomori ................ 600/440 |
| 5,454,371 A | * | 10/1995 | Fenster et al. ............. 600/443 |
| 5,920,317 A | | 7/1999 | McDonald |
| 5,928,151 A | | 7/1999 | Hossack et al. |
| 6,167,296 A | * | 12/2000 | Shahidi ....................... 600/427 |
| 6,245,017 B1 | * | 6/2001 | Hashimoto et al. ......... 600/447 |
| 6,346,940 B1 | * | 2/2002 | Fukunaga ................... 345/427 |
| 6,351,678 B1 | * | 2/2002 | Borders ....................... 700/83 |
| 6,563,941 B1 | * | 5/2003 | O'Donnell et al. ......... 382/131 |
| 6,599,244 B1 | * | 7/2003 | Epps et al. .................. 600/437 |
| 6,675,038 B2 | * | 1/2004 | Cupples et al. ............. 600/424 |

OTHER PUBLICATIONS

"SONOLINE Versa Plus Ultrasound Imaging System Operating Instructions," Siemens Medical Systems, Inc., pp. 6-37 to 6-40 (Oct. 1997).
"Registration of 3D Ultrasound Images to Surface Models of the Heart," Pieper et al., Proceedings of the Interface to Real & Virtual Worlds, pp. 1-6 (May 1997).
"Medical Diagnostic Ultrasound System and Method for Scanning Plane Orientation," U.S. Appl. No. 09/517,014, filed Mar. 2, 2000, inventors: John I. Jackson and John A. Hossack.

* cited by examiner

Primary Examiner—Francis J. Jaworski

(57) ABSTRACT

The preferred embodiments described herein relate to three-dimensional pictograms and indicators for use with medical images. In one embodiment, a three-dimensional pictogram representing anatomy shown in a medical image is displayed along with a marker that represents a medical instrument used to create the medical image. A user can adjust an orientation of the marker with respect to the three-dimensional pictogram. In another embodiment, a set of three-dimensional pictograms of anatomy is displayed. A user can select one of the three-dimensional pictograms for display near a medical image and rotate the three-dimensional pictogram. In another embodiment, a saved three-dimensional pictogram is retrieved, and a user can rotate the three-dimensional pictogram starting from the orientation shown in the retrieved pictogram. In yet another embodiment, a three-dimensional pictogram is used as an indicator for a three-dimensional medical image. Other embodiments are provided, and each of the embodiments described herein can be used alone or in combination with one another.

36 Claims, 14 Drawing Sheets

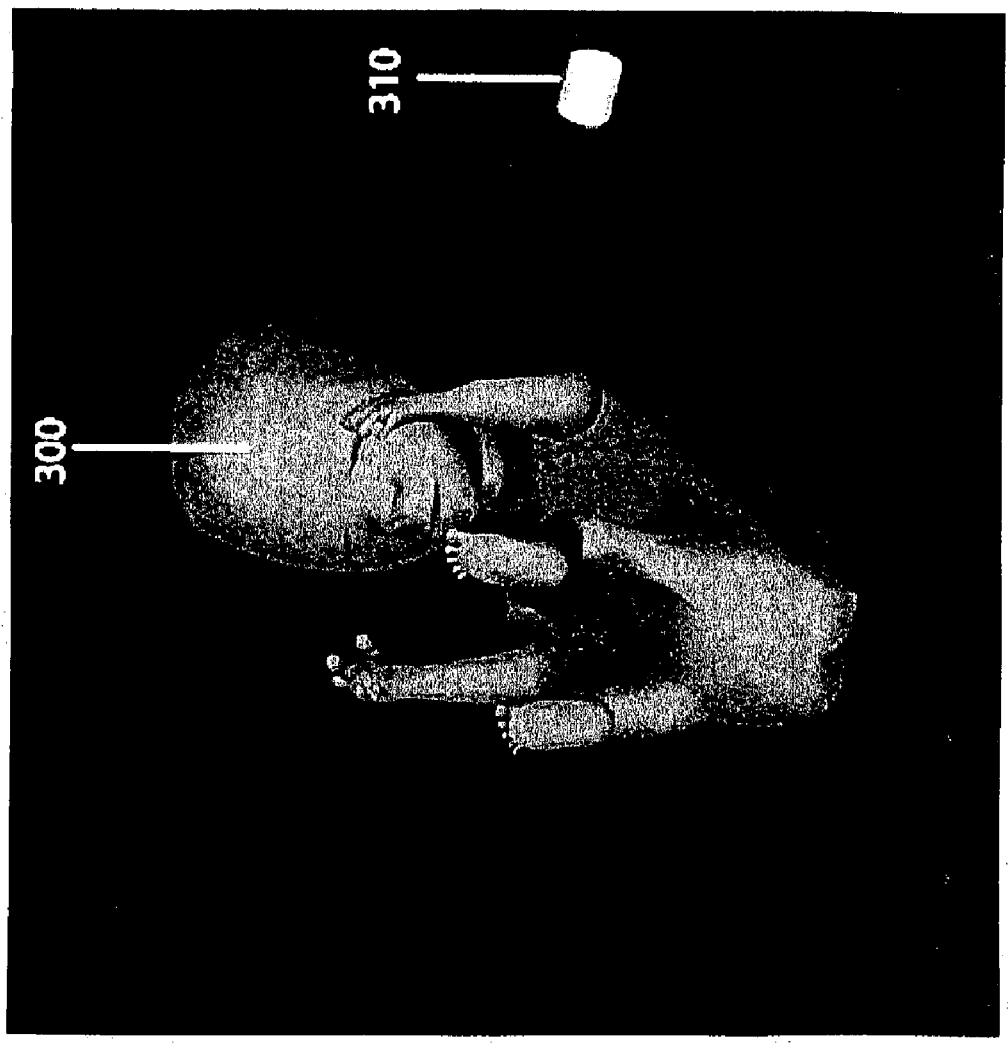
Fig. 4-B

THREE-DIMENSIONAL PICTOGRAMS FOR USE WITH MEDICAL IMAGES

BACKGROUND

When capturing a medical image, it is often desired to label the image to indicate and describe the anatomical structure under evaluation. Some imaging systems allow a user to label a medical image with textual remarks known as annotations or with graphical symbols known as pictograms. On some systems, pictograms are implemented as two-dimensional outlines that offer limited information about the anatomy under evaluation. Many two-dimensional pictograms do not define direction and are useful only as a generic label for anatomy. In some systems, a series of two-dimensional pictograms offering different outlines of the same anatomy (e.g., right kidney, left kidney) are presented for user selection. A user can also place a dash next to the two-dimensional pictogram to indicate the general position and orientation of the transducer probe. In at least one ultrasound imaging system, a displayed two-dimensional fetal pictogram can be rotated about a single axis to indicate the general placement of the fetus in utero, and a marker indicating transducer probe location can be positioned near the two-dimensional pictogram and rotated about a single axis to indicate where the transducer was in relation to the scan.

There is a need for a method and system for labeling a medical image with a pictogram that provides users with more information about the anatomical structure under evaluation.

SUMMARY

The present invention is defined by the following claims, and nothing in this section should be taken as a limitation on those claims.

By way of introduction, the embodiments described below relate to three-dimensional pictograms for use with medical images. In one embodiment, a three-dimensional pictogram representing anatomy shown in a medical image is displayed along with a marker that represents a medical instrument used to create the medical image. A user can adjust an orientation of the marker with respect to the three-dimensional pictogram. In another embodiment, a set of three-dimensional pictograms of anatomy is displayed. A user can select one of the three-dimensional pictograms for display near a medical image and rotate the three-dimensional pictogram. In another embodiment, a saved three-dimensional pictogram is retrieved, and a user can rotate the three-dimensional pictogram starting from the orientation shown in the retrieved pictogram. In yet another embodiment, a three-dimensional pictogram is used as an indicator for a three-dimensional medical image. Other embodiments are provided, and each of the embodiments described herein can be used alone or in combination with one another.

The embodiments will now be described with reference to the attached drawings.

BRIEF DESCRIPTION OF THE DRAWINGS

FIGS. 4A and 4B are illustrations of a transducer marker in various orientations around a three-dimensional pictogram of an embodiment.

DETAILED DESCRIPTION OF THE PRESENTLY PREFERRED EMBODIMENTS

Figure 1:
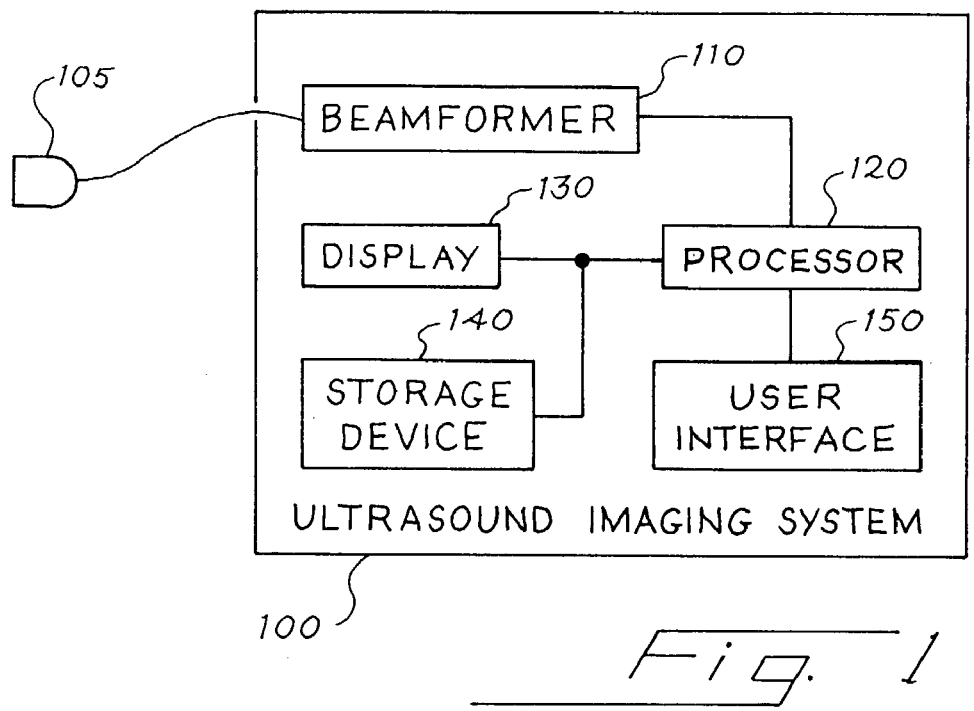
FIG. 1 is a block diagram of a medical diagnostic ultrasound imaging system of an embodiment.

Turning now to the drawings, FIG. 1 is a block diagram of a medical diagnostic ultrasound imaging system 100 that will be used to illustrate the operation of the embodiments described below. While an ultrasound system and ultrasound images are used in this illustration, it should be noted that other types of medical image acquisition devices and medical images can be used. As shown in FIG. 1, the ultrasound system 100 comprises a transducer probe 105, a beamformer 110, a processor 120, a display device 130, a storage device 140, and a user interface 150. The term "processor" broadly refers to the appropriate hardware and/or software components (i.e., computer-readable program code) of the ultrasound system 100 that can be used to implement the functionality described herein. The storage device 140 (i.e., computer-usable media) is suitable for storing digital images and can take the form, for example, of a solid-state volatile or non-volatile memory device or a permanent or removable optical or magnetic disk. The user interface 150 can include, for example, physical knobs, buttons, or keys that a user can physically manipulate on a control panel; soft buttons displayed on the display device 130 that a user can select with a pointing device or by touching the displayed button if the display device 130 is touch-sensitive; or a microphone through which a user can voice commands. The ultrasound system 100 can comprise additional components (such as a network connector), which are not shown in FIG. 1 for simplicity.

In operation, a sonographer uses the user interface 150 to select a study type. Study types are typically classified according to the general anatomy to be imaged. Examples of study types include, but are not limited to, abdomen, breast, cerebrovascular, digital, fetal echo, gynecological, musculoskeletal, obstetrics, pediatric abdomen, pediatric hip, pelvis, penile, peripheral vascular—arteries, peripheral vascular—veins, prostate, renal, superficial musculoskeletal, testis, and thyroid. A study type determines settings used in the transmit, receive, and/or processing operations to affect how the medical image is acquired.

During an ultrasound examination, the sonographer contacts the transducer probe 105 with a patient, and the ultrasound system 100 acquires an ultrasound image in accordance with the selected study type. In general, the ultrasound system's processor 120 causes the beamformer 110 to apply a voltage to the transducer 105 to cause it to vibrate and emit an ultrasonic beam into the portion of the patient's body in contact with the transducer 105. Ultrasonic energy reflected from the patient's body impinges on the transducer 105, and the resulting voltages created by the transducer 105 are received by the beamformer 110. The processor 120 processes the sensed voltages to create an ultrasound image and displays the image on the display device 130.

Figure 2:
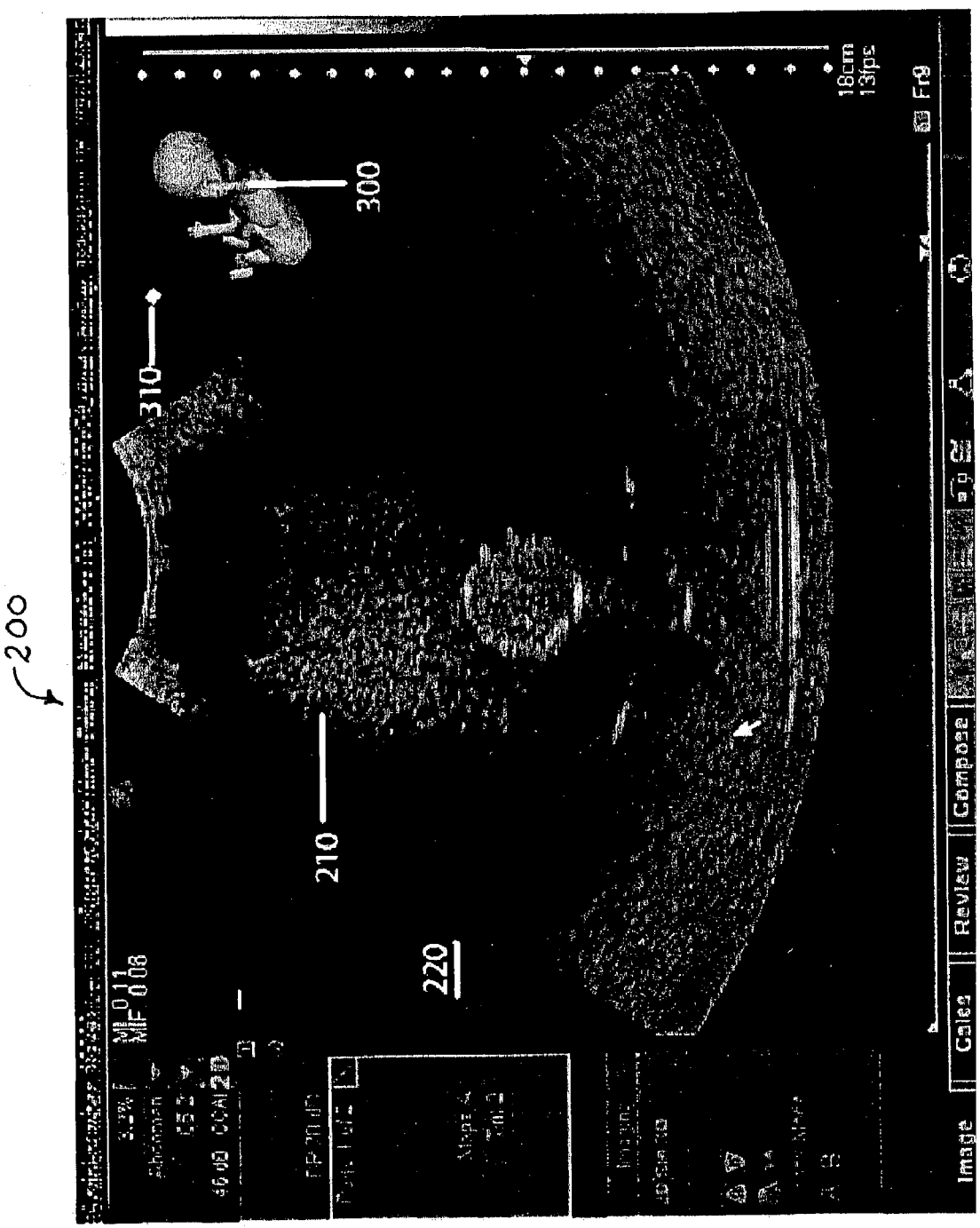
FIG. 2 is an illustration of a display of an embodiment.

FIG. 2 is an illustration of an output 200 of the display device 130 after an ultrasound image has been generated.

The output 200 displays an ultrasound image 210 and an area 220 for displaying information about the image 210. Area 220 is provided around the ultrasound image 210 so that the information will not obscure the ultrasound image 210. If desired, the information can be at least partially positioned on top of the ultrasound image 210.

As shown in FIG. 2, one form of information that can be displayed is a three-dimensional pictogram 300. As used herein, the term "pictogram" refers to a graphic that represents the anatomy shown in the ultrasound image 210. A pictogram helps identify and describe that anatomy under evaluation to a person who later reviews the ultrasound image 210. Pictograms include, but are not limited to, graphics of the following anatomy: fetus, arm, foot, leg, liver, pancreas, spleen, biliary, heart, kidney, supine, prone, bladder, uterus, ovary, groin, neck, face, head, thigh, knee, ankle, breast, thyroid, testis, wrist, hip, bone, joint, shoulder, elbow, hand, and prostate. In this embodiment, the pictogram 300 is a three-dimensional pictogram. As used herein, the term "three-dimensional pictogram" refers to a rendered graphic that appears to have extension in depth. Preferably, the pictogram 300 is rotatable about at least two axes (e.g., two or more of the x, y, and/or z axes) for viewing the pictogram from different angles, and most preferably about all three axes to position the three-dimensional pictogram 300 in any orientation (i.e., the pictogram 300 preferably has three rotation degrees of freedom). It should be noted that other types of identification can be used along with a three-dimensional pictogram. For example, textual remarks describing the anatomy under investigation ("annotations") and a two-dimensional pictogram can be used in conjunction with a three-dimensional pictogram. It should also be noted that while FIG. 2 shows a single ultrasound image 210 presented along with a single three-dimensional pictogram 300, two or more ultrasound images can be displayed simultaneously, each with a respective three-dimensional pictogram.

To display a pictogram in this embodiment, the user either selects a displayed pictogram icon or presses a pictogram key on a keyboard. A set of three-dimensional pictograms representing various anatomy (a set of "base models") is then displayed for user selection. As used herein, the term "set" refers to a group of one or more. In this embodiment, the set of base models presented for user selection is determined by the study type selected by the user. After the user selects a study type, a corresponding application package is loaded that contains a library of pictograms associated with that study type. For example, an Abdominal Application Package can contain pictograms for abdominal and renal exams. To select a pictogram from the displayed set of base models, the user turns a rotary knob (or another type of user interface element, such as arrow keys on a keyboard) to cycle through the displayed base models. When the cursor is over the desired pictogram, the user presses the button, and the selected three-dimensional pictogram 300 is displayed in area 220 near the ultrasound image 210. In this embodiment, a transducer marker 310 is automatically positioned near the three-dimensional pictogram 300 when the three-dimensional pictogram 300 is displayed. In an alternate embodiment, the transducer marker 310 is displayed in response to a request from the user (e.g., after the user either selects a displayed transducer marker icon or presses a transducer marker key on a keyboard or after the user indicates that he is done rotating the three-dimensional pictogram 300). The transducer marker 310 will be described in more detail below.

Figure 3A:
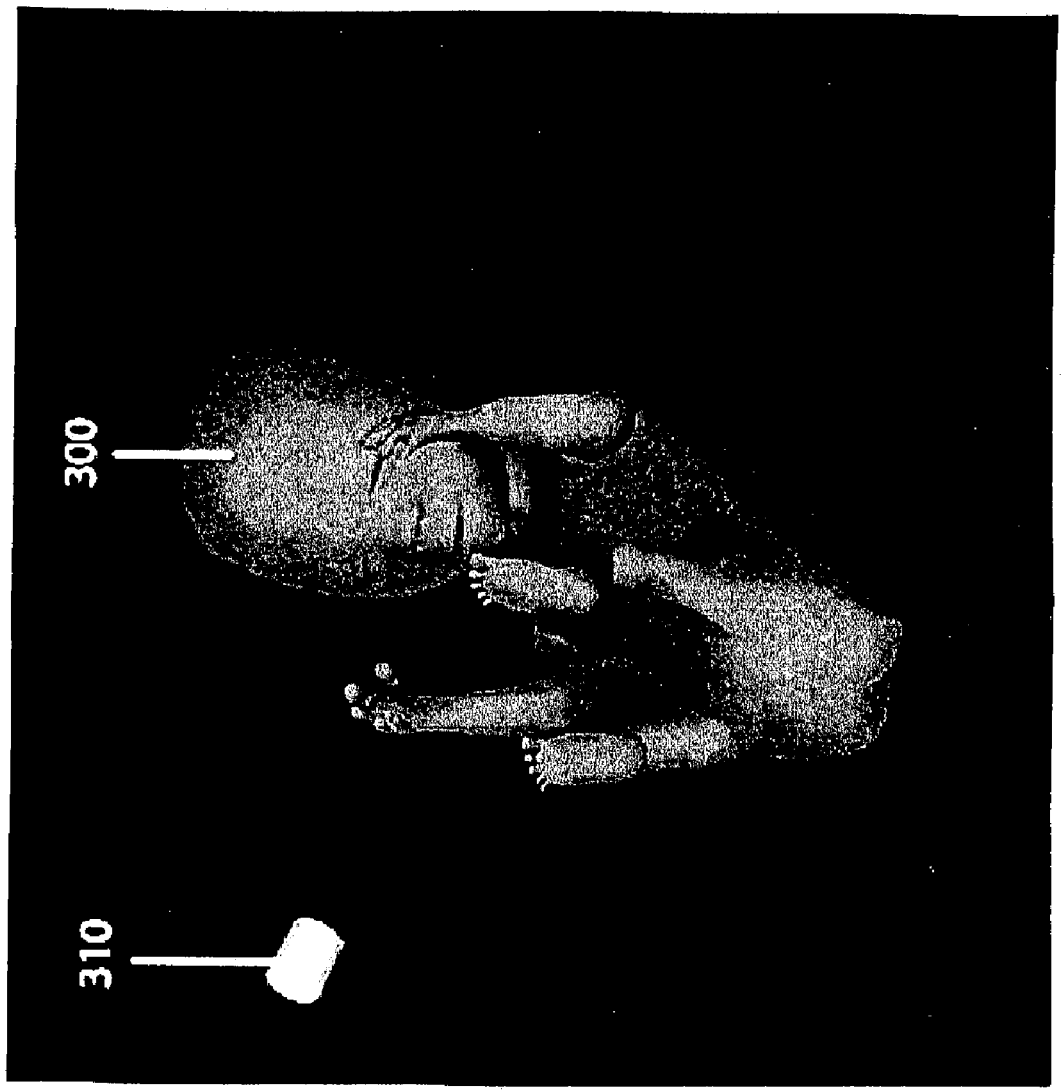
FIGS. 3A–3G are illustrations of a three-dimensional pictogram of an embodiment in various orientations.
Figure 3B:
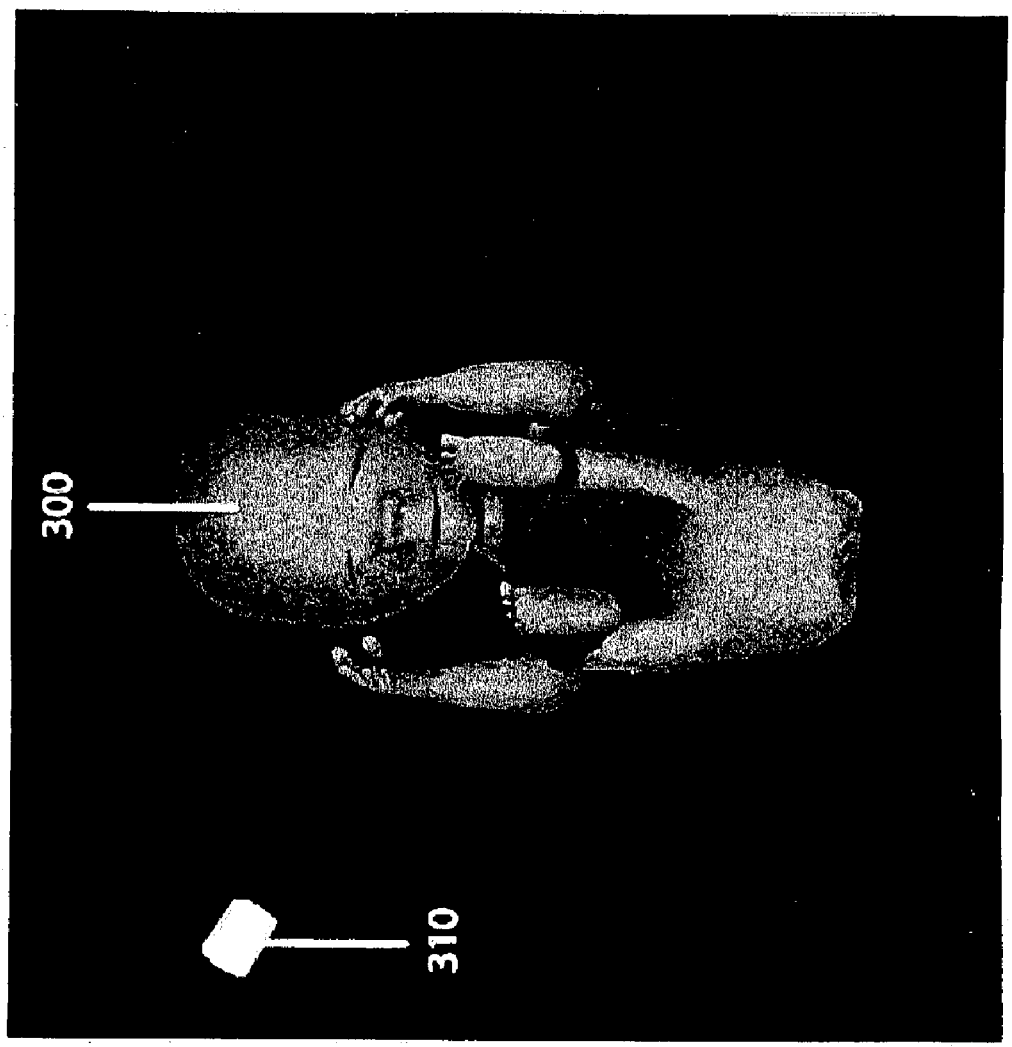
Figure 3C:
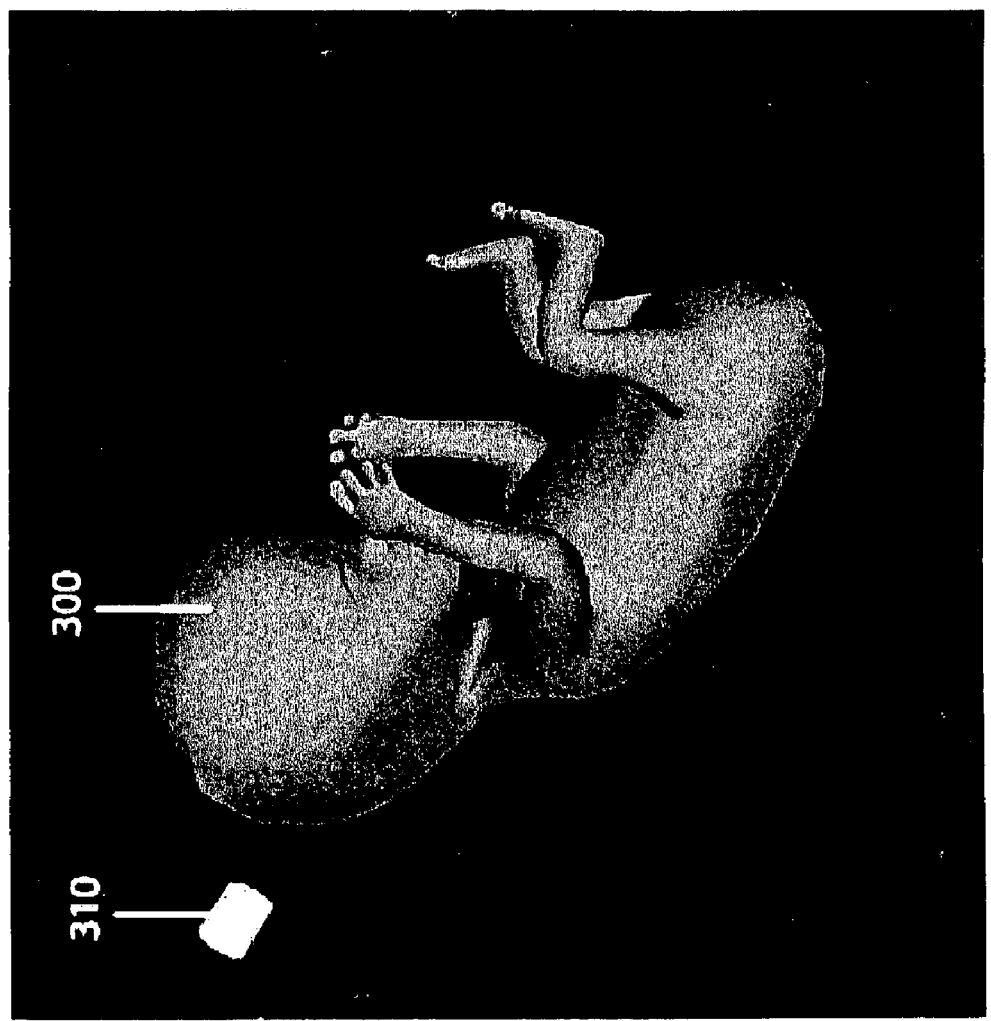
Figure 3D:
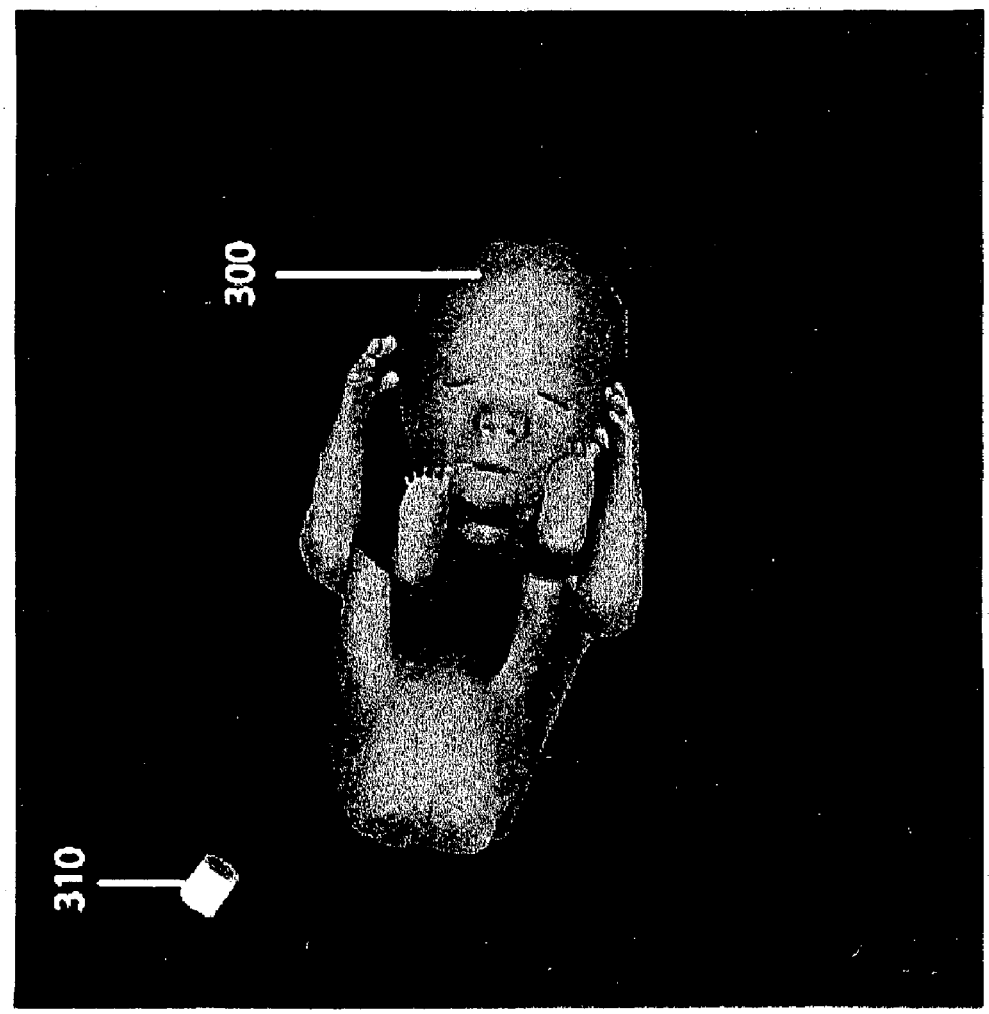
Figure 3E:
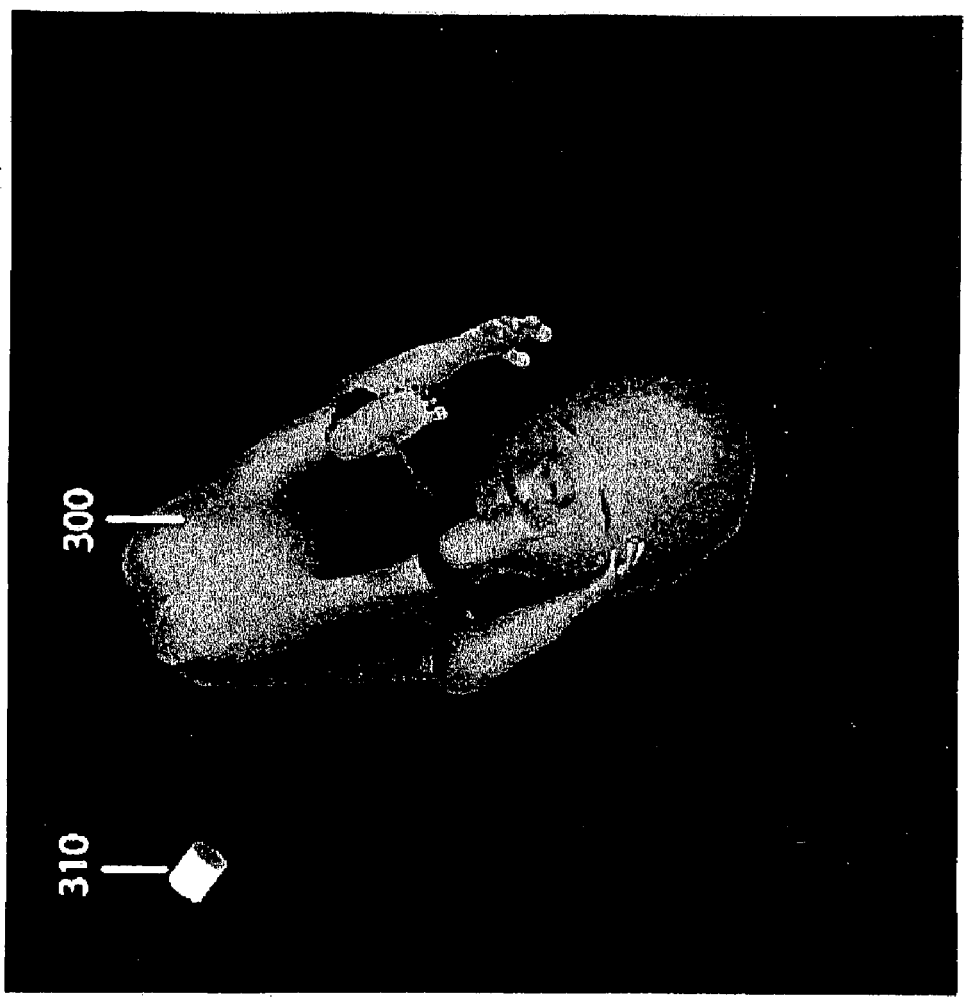
Figure 3F:
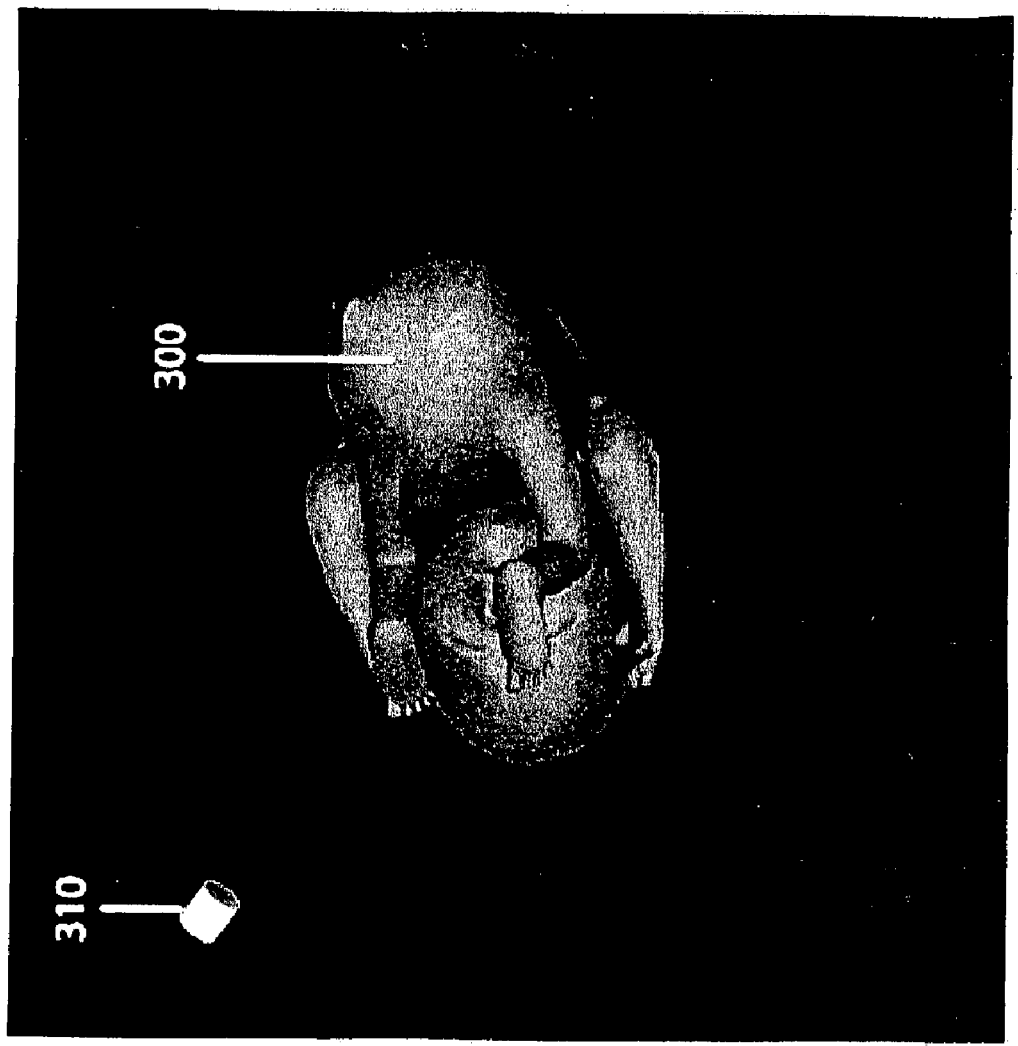
Figure 3G:
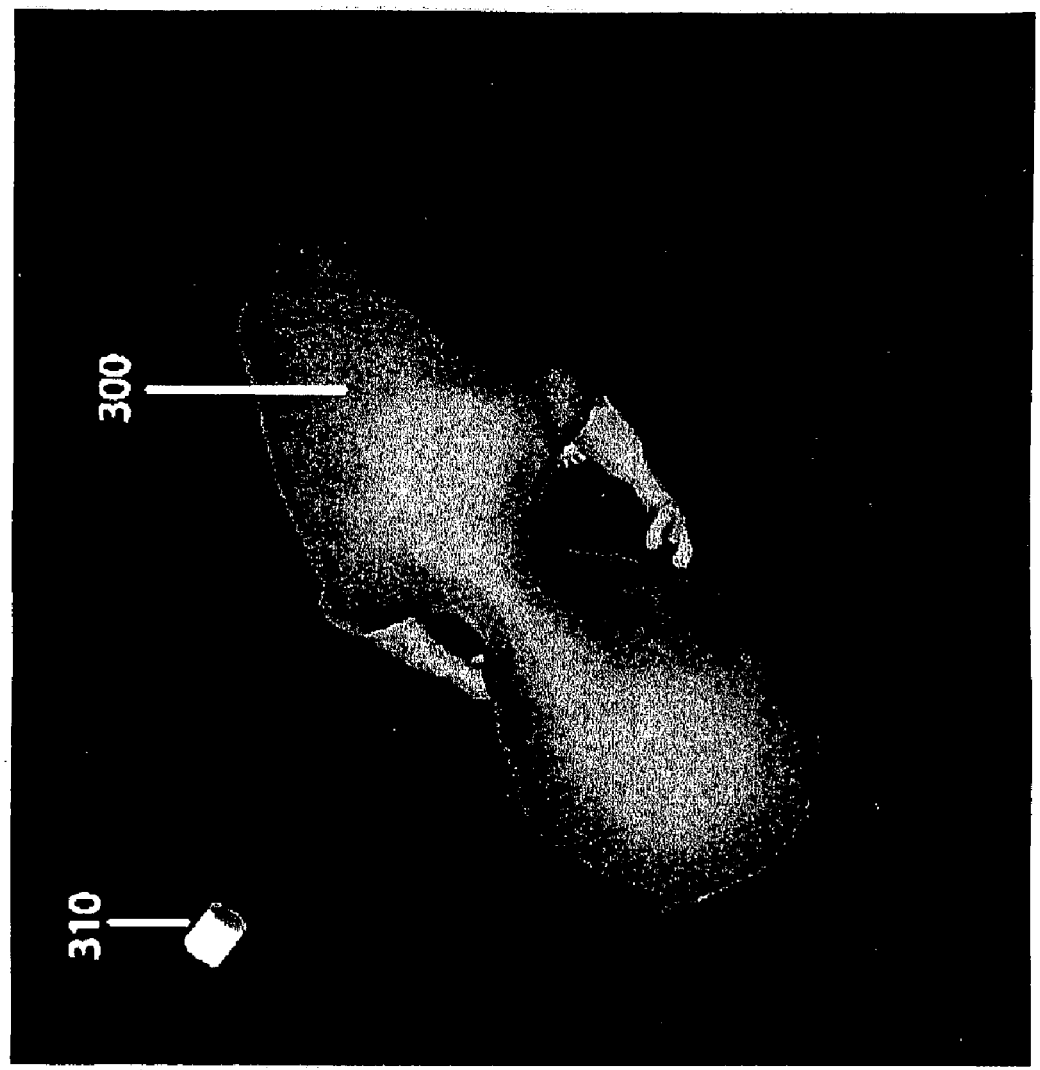

After the base model has been selected and displayed, the user can rotate the three-dimensional pictogram 300 to represent the direction of acquisition. In this embodiment, the three-dimensional pictogram 300 is rotatable about all three axes, allowing the user to position the three-dimensional pictogram 300 in any desired orientation. In other embodiments, rotation of the three-dimensional pictogram 300 can be limited to selected orientations, or the rotation of the three-dimensional pictogram 300 can be limited about one or two axes. In operation, the user rotates a trackball, and the three-dimensional pictogram 300 is rotated to follow the trackball based on its degree of change. Turning again to the drawings, FIG. 3A is an illustration of the three-dimensional pictogram 300 in a first orientation. As the user rotates the trackball to the right, the three-dimensional pictogram 300 also rotates to the right. FIGS. 3B and 3C show the three-dimensional pictogram 300 after various degrees of rotation. In FIGS. 3A–C, the three-dimensional pictogram 300 was rotated about a vertical axis. FIGS. 3D–F show the three-dimensional pictogram 300 being rotated from the orientation shown in FIG. 3B about an axis running through the paper. FIG. 3G shows the three-dimensional pictogram 300 rotated about another axis.

Figure 4A:
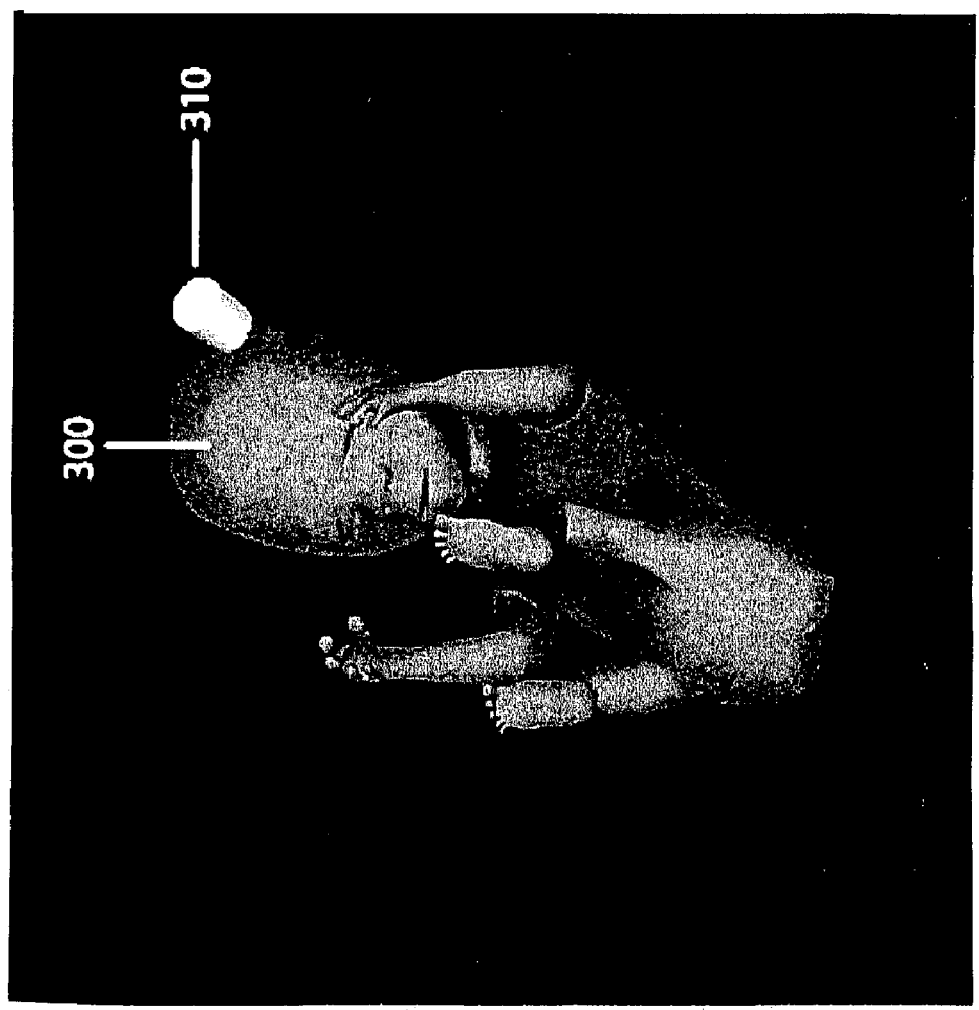

As mentioned above, a transducer marker 310 is positioned near the three-dimensional pictogram 300. As used herein, the term "transducer marker" refers to a graphical representation of the medical instrument used to generate the medical image. In this embodiment, a user can adjust the location of the transducer marker 310 with respect to the three-dimensional pictogram 300 to indicate the orientation of the transducer to the anatomy. As the user moves the trackball, the transducer marker 310 orbits around the three-dimensional pictogram 300 (e.g., from the position shown in FIG. 3A to the positions shown in FIGS. 4A and 4B). It should be noted that while the transducer marker 310 remained fixed as the three-dimensional pictogram 300 was rotated in the illustrations in FIGS. 3A–G, the transducer marker 310 can rotate along with the three-dimensional pictogram 300 as it is rotated. It should also be noted that a three-dimensional pictogram 300 can be displayed without a transducer marker 310. In this situation, the orientation of the three-dimensional pictogram 300 alone can provide an indication of where the transducer was positioned.

In this embodiment, the user has the ability to re-adjust the three-dimensional pictogram 300 or the transducer marker 310. For example, if the user wishes to re-adjust the three-dimensional pictogram 300 after adjusting the transducer marker 310, the user can reselect the three-dimensional pictogram 300 and modify its orientation. The user can also hide (i.e., remove the display of) the three-dimensional pictogram 300 and/or the transducer marker 310.

There are several advantages associated with using a three-dimensional pictogram as compared to a two-dimensional pictogram. Two-dimensional pictograms generally do not define direction and merely denote general information that can be used as a generic label for anatomy. Three-dimensional pictograms extend this basic functionality by providing more meaningful data about the acquired image. Unlike a two-dimensional pictogram, a user can rotate a three-dimensional pictogram in any direction to more accurately represent the direction of acquisition and provide a better representation of the actual scan. Because they are directly manipulatable, three-dimensional pictograms offer an infinite number of possibilities regarding directional and positional information and provide more information about the anatomy under evaluation. Additionally, three-dimensional pictograms provide an improved representation of the anatomy acquired by providing a graphic that has a higher quality look and feel and that is easier for a user to understand. Further, unlike two-dimensional pictograms which are presented for user selection as a finite set of multiple, non-rotatable outlines in various orientations, these embodiments allow a user to select a single base model that can be manipulated by the user to any desired orientation. In this way, these embodiments allow the user to create an infinite set of images by leveraging a few base models such as, for example, liver, lungs, brain, and fetus.

Figure 5:
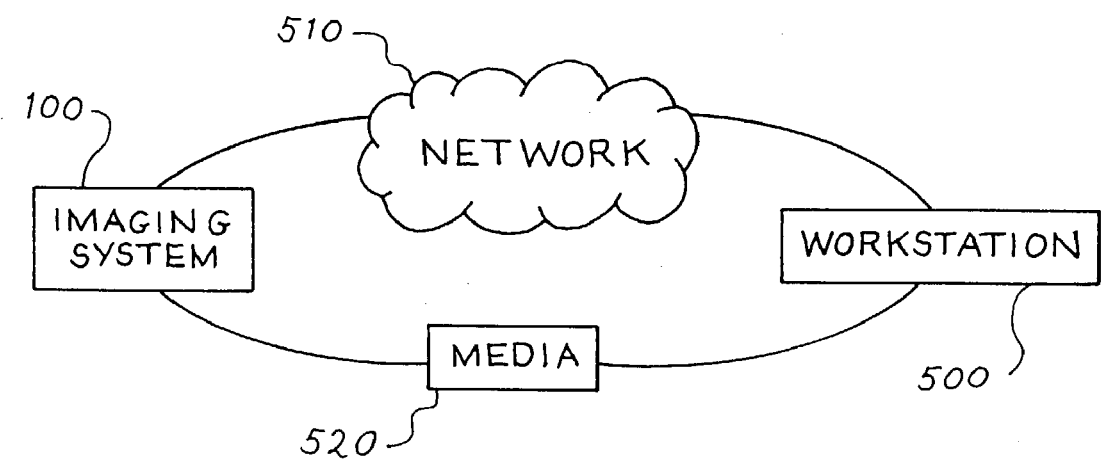
FIG. 5 is an illustration of an imaging network of an embodiment.

In the previous illustration, the ultrasound image 210, three-dimensional pictogram 300, and transducer marker 310 were displayed on the display device 130 of the ultrasound system 100. In addition to being displayed, the ultrasound image 210, three-dimensional pictogram 300, and transducer marker 310 can be saved in digital form in the storage device 140 in the ultrasound system 100 for later review or post-processing on the ultrasound system 100 or on a workstation 500 (see FIG. 5). A workstation is a computer comprising a display device, a user interface, and a processor that runs image review software that allows a user to retrieve a stored image and perform measurements and other actions on that image. With reference to FIG. 5, the ultrasound image 210, three-dimensional pictogram 300, and transducer marker 310 can be sent from the ultrasound system 100 to the workstation 500 via a network 510 (e.g., the Internet, a hospital or clinic intranet, etc.) or removable media 520 (e.g., a CD-ROM, a memory stick, an MO disk, etc.). Preferably, the images are saved and transferred according to the DICOM format.

During image review (either on the ultrasound system 100 or on the workstation 500), another user (e.g., another sonographer or a physician) views an image saved during an examination. When reviewing the image, the user can hide or turn off the display of the three-dimensional pictogram 300 and/or transducer marker 310. In addition, when the three-dimensional pictogram 300 and/or transducer marker 310 are recovered, the orientation of the three-dimensional pictogram 300 and/or transducer marker 310 is also recovered, and the user can rotate the three-dimensional pictogram 300 and/or transducer marker 310 from its saved orientation. For example, if a reviewing physician determines that the transducer marker 310 is at the wrong location on the three-dimensional pictogram 300, the physician can change the location of the transducer marker 310 to more accurately depict the actual scan. While this manipulation can be performed on the saved version of the image, it may be preferred to allow this manipulation only on a copy of the saved image to retain an immutable version of the sonographer's original data.

Post-processing recovery and manipulation of three-dimensional pictograms provide another advantage over systems that use two-dimensional pictograms. While prior systems allow post-processing recovery of two-dimensional pictograms, those systems only allow a new two-dimensional pictogram to be added—a recovered two-dimensional pictograms cannot be altered or modified. Accordingly, if the user finds that the recovered two-dimensional pictogram is not accurate, the user would need to add a new two-dimensional pictogram and set-up the transducer marker from scratch. In contrast, by allowing the user to re-adjust the three-dimensional pictogram 300 and/or transducer marker 310 from the state in which it was saved, this embodiment saves steps in the user's workflow. The reviewing user can simply adjust the three-dimensional pictogram 300 and/or transducer marker 310 from where the prior user left off.

Turning now to another embodiment, three-dimensional ultrasound and other medical images can be used to provide a physician with views that are not normally achievable with traditional two-dimensional images. U.S. Pat. No. 5,928,151, which is hereby incorporated by reference, describes a system and method that can be used to generate three-dimensional ultrasound images. In operation, ultrasound data is collected over an area of the patient by, for example, sweeping a transducer probe over a portion of a patient's body. The generated data set is stored, and a user can select a slicing plane at any angle through the data set through a post-processing activity, for example, on the workstation 500. A three-dimensional ultrasound image "under" the slicing plane would then be created from the data set and displayed. The three-dimensional ultrasound image would give the appearance that the anatomy "above" the slicing plane was "sliced off."

Because the sliced three-dimensional image is independent of probe position, a user can have difficulty orienting himself to the displayed volume. To assist the user, some ultrasound systems display a cone and a plane cutting through the cone to visualize the slicing plane's position and orientation in the ultrasound volume. Other ultrasound systems display a quad-screen format with three-dimensional images in three different slicing planes in three of the quadrants and a "reference cube" in the fourth quadrant. The reference cube displays the orientation of the images shown in the three quadrants to one another. Other systems use a bounding box and a pyramid to indicate general direction information.

Figure 6A:
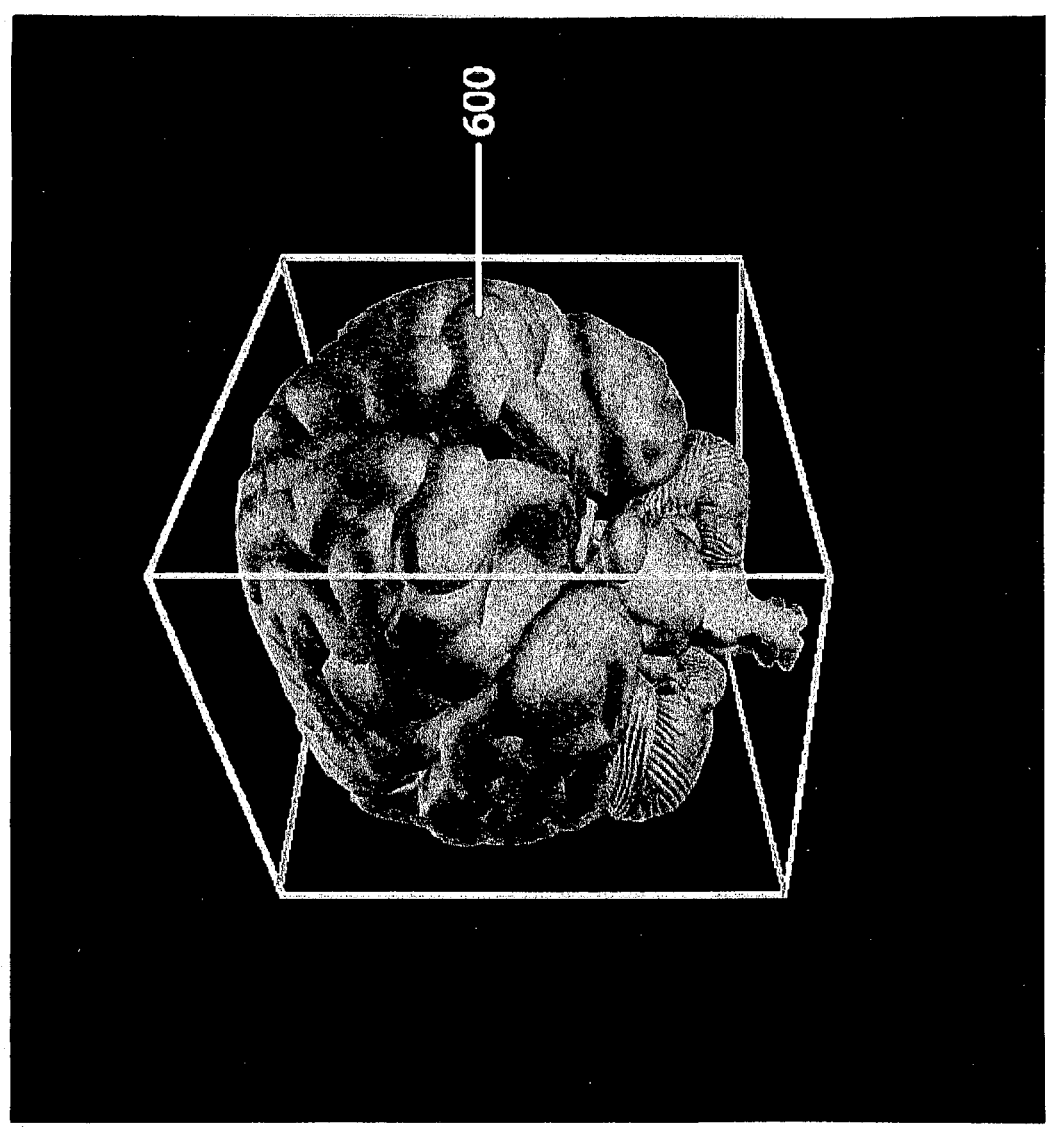
FIGS. 6A–6C are illustrations of a three-dimensional pictogram of an embodiment used to indicate a slicing plane's position and orientation in a three-dimensional medical image.
Figure 6B:
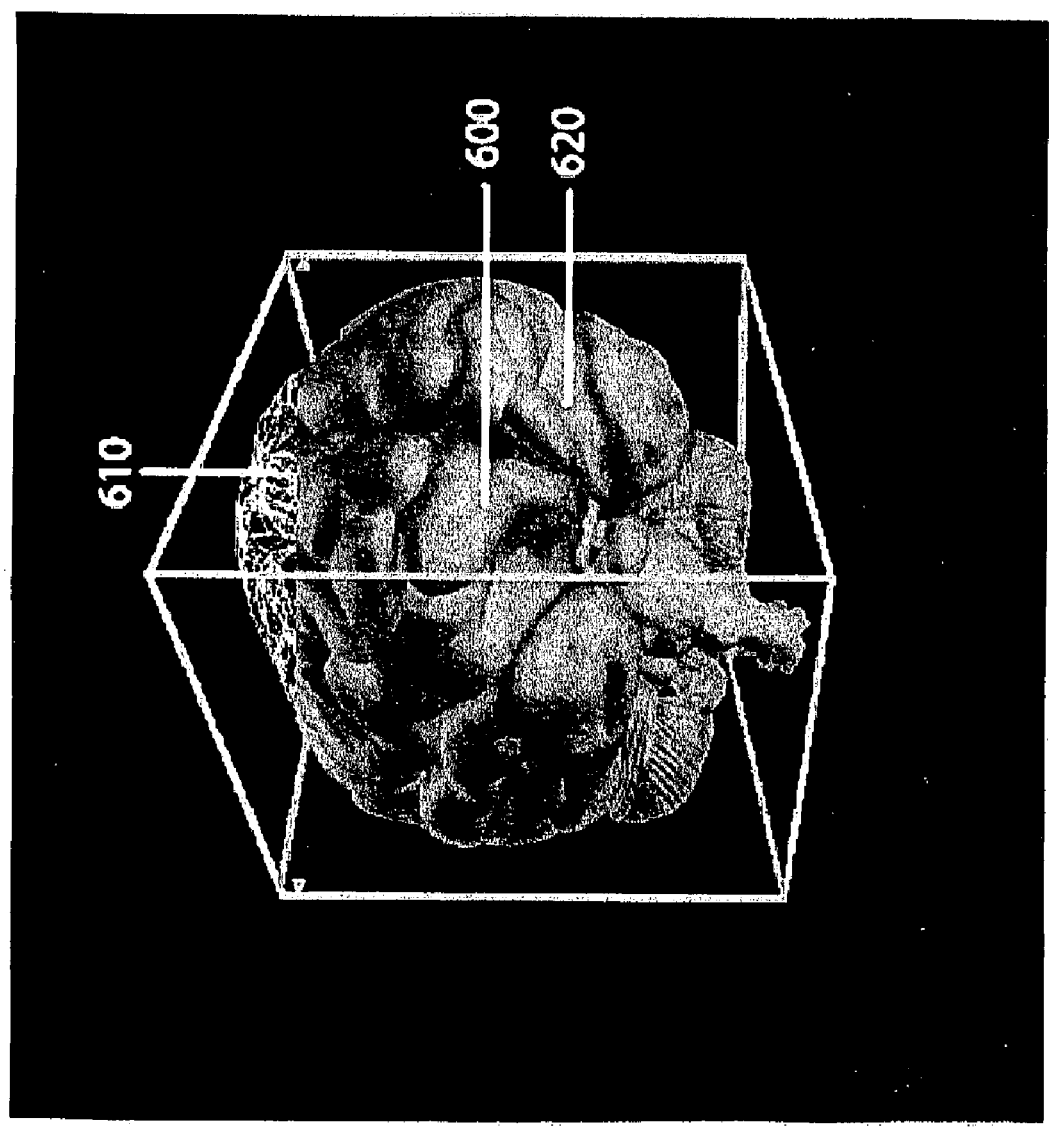
Figure 6C:
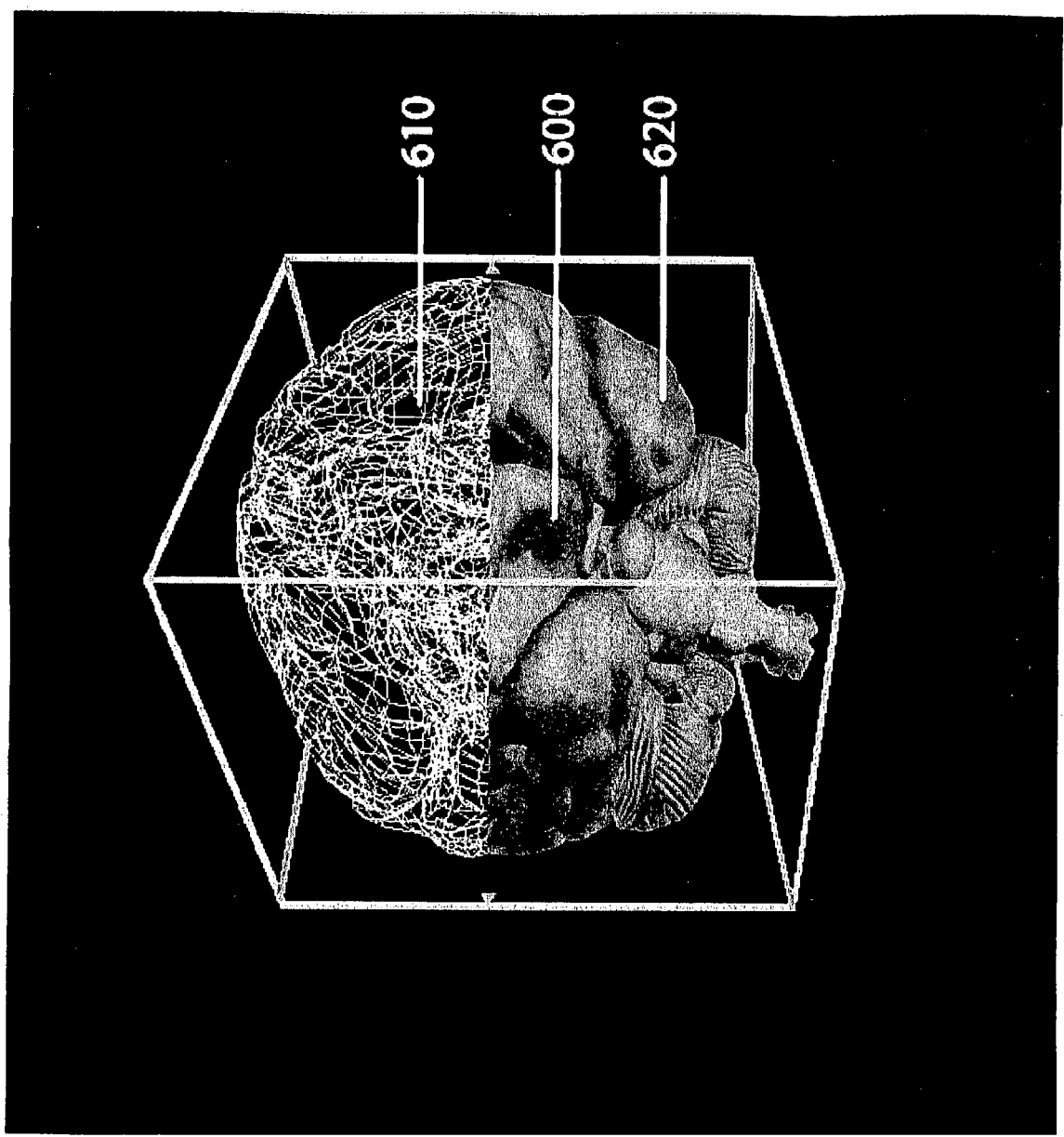

In this embodiment, instead of using a cone, a reference cube, or a bounding box, a three-dimensional pictogram is displayed near a three-dimensional image to assist the user visualize the slicing plane's position and orientation. FIG. 6A shows a three-dimensional pictogram of a brain 600. All of the three-dimensional pictogram 600 is shown as a solid, graphically-rendered representation. The user selects a slicing plane on the three-dimensional pictogram 600, and the slicing plane divides the three-dimensional pictogram 600 into a first portion and a second portion. As shown in FIG. 6B, the first portion 610 is displayed as a wire frame instead of a graphical rendition, and the second portion 620 remains a solid, graphically-rendered representation of the brain. The graphical rendition shows the user what is being displayed in the three-dimensional ultrasound image, while the wire frame shows the user what volume is not being displayed. This not only orients the user to the slicing plane's position and orientation, but it also provides the user with information about the portion of the anatomy that is not being shown. FIG. 6C shows the three-dimensional pictogram 600 with the slicing plane at a lower location in the brain. As with the above embodiments, a user can be presented with a set of base models for user selection. The set of base models can be based on study type.

Using a three-dimensional pictogram as an indicator of the scan provides an improvement over cone indicators, reference cubes, or bounding boxes because it adds anatomical information, which gives the user a better understanding of what he is looking at. Additionally, using a wire-frame for the portion of the image that is sliced away provides the user with a better perspective of the acquired image and feedback as to the remainder of the anatomy.

As noted above, the functionality described herein can be performed by executing computer-readable program code stored on computer-usable media (e.g., one or more memory devices or disk drives). The computer-readable program code can be located in any suitable location, such as in the ultrasound system 100, in the workstation 500, or in another component (not shown) in the network 510.

Finally, as also noted above, although ultrasound images were used to illustrate the embodiments described herein, any type of medical image can be used. Medical images include images generated from any imaging modality including, but not limited to, ultrasound, computed tomography (CT), magnetic resonance imaging (MRI), computed radiography, magnetic resonance, angioscopy, color flow Doppler, cystoscopy, diaphanography, echocardiography, fluoresosin angiography, laparoscopy, magnetic resonance angiography, positron emission tomography, single-photon emission computed tomography, x-ray angiography, computed tomography, nuclear medicine, biomagnetic imaging, culposcopy, duplex Doppler, digital microscopy, endoscopy, fundoscopy, laser surface scan, magnetic resonance spectroscopy, radiographic imaging, thermography, and radio fluroscopy. The following claims should not be limited to a specific type of medial image unless explicitly recited therein.

It is intended that the foregoing detailed description be understood as an illustration of selected forms that the invention can take and not as a definition of the invention. It is only the following claims, including all equivalents, that are intended to define the scope of this invention.

What is claimed is:

1. A method for labeling a medical image with a three-dimensional pictogram, the method comprising:
   (a) displaying a medical image;
   (b) displaying a three-dimensional pictogram representing anatomy shown in the medical image;
   (c) displaying a marker near but not through the three-dimensional pictogram, the marker representing a medical instrument used to create the medical image; and
   (d) adjusting an orientation of the marker relative to the orientation of the three-dimensional pictogram in accordance with an manual adjustment received from a user via a user interface.

2. The method of claim 1, wherein the marker is manipulatable with three rotation degrees of freedom around the three-dimensional pictogram.

3. The method of claim 1 further comprising rotating the three-dimensional pictogram.

4. The method of claim 3, wherein the three-dimensional pictogram is rotatable with three degrees of freedom.

5. The method of claim 1 further comprising, before (b), displaying a set of three-dimensional pictograms for user selection.

6. The method of claim 5, wherein the set of three-dimensional pictograms is determined based on study type.

7. The method of claim 1 further comprising:
   (e) hiding the three-dimensional pictogram and marker.

8. A method for labeling a medical image with a three-dimensional pictogram, the method comprising:
   (a) displaying a set of three-dimensional pictograms of anatomy;
   (b) receiving a user selection of a three-dimensional pictogram from the displayed set;
   (c) displaying a medical image;
   (d) displaying the selected three-dimensional pictogram near the medical image; and
   (e) rotating the three-dimensional pictogram independent of the displayed medical image in accordance with a manual adjustment received from a user via a user interface.

9. The method of claim 8, wherein the set of three-dimensional pictograms is determined based on study type.

10. The method of claim 8, wherein the selected three-dimensional pictogram is rotatable with three degrees of freedom.

11. The method of claim 8 further comprising:
    (f) displaying a marker near the selected three-dimensional pictogram, the marker representing a medical instrument used to create the medical image.

12. The method of claim 11 further comprising:
    (g) adjusting an orientation of the marker.

13. The method of claim 8 further comprising:
    (f) hiding the selected three-dimensional pictogram.

14. A method for labeling a medical image with a three-dimensional pictogram, the method comprising:
    (a) displaying a medical image;
    (b) displaying a three-dimensional pictogram representing anatomy shown in the medical image;
    (c) rotating the three-dimensional pictogram to a first orientation;
    (d) saving the medical image and three-dimensional pictogram;
    (e) retrieving the saved medical image and three-dimensional pictogram; and
    (f) rotating the three-dimensional pictogram, the rotation starting from the first orientation independent of the displayed medical image in accordance with a manual adjustment received from a user via a user interface.

15. The method of claim 14 further comprising, before (f), creating a copy of the saved medical image and three-dimensional pictogram, and wherein (f) comprises rotating the three-dimensional pictogram on the copy.

16. The method of claim 14 further comprising providing the saved medical image and three-dimensional pictogram to a workstation, and wherein (f) is performed on the workstation.

17. The method of claim 16, wherein the saved medical image and three-dimensional pictogram are provided to the workstation via a network.

18. The method of claim 16, wherein the saved medical image and three-dimensional pictogram are provided to the workstation via a removable media device.

19. The method of claim 16 further comprising, before (d), displaying a marker near the three-dimensional pictogram and adjusting an orientation of the marker to a second orientation, the marker representing a medical instrument used to create the medical image, wherein the marker is saved with the medical image and three-dimensional pictogram, and wherein the method further comprises retrieving the saved marker with the saved medical image and three-dimensional pictogram and adjusting the marker, the adjustment starting from the second orientation.

20. A method for labeling a medical image with a three-dimensional pictogram, the method comprising:
    (a) displaying a three-dimensional medical image;
    (b) displaying a graphically-rendered three-dimensional pictogram representing anatomy shown in the three-dimensional medical image;
    (c) receiving from a user a slicing plane through the three-dimensional medical image;
    (d) displaying a medical image in accordance with the user-selected slicing plane; and
    (e) displaying a portion of the three-dimensional pictogram as a wire frame instead of a graphically-rendered representation of the anatomy, wherein the remaining portion of the three-dimensional pictogram is still displayed as a graphically rendered representation of the anatomy and not as a wire frame the wire frame portion corresponding to a sliced-off portion of the three-dimensional medical image.

21. The method of claim 20 further comprising, before (a), displaying a set of three-dimensional pictograms for user selection.

22. The method of claim 21, wherein the set of three-dimensional pictograms is determined based on study type.

23. A system for labeling a medical image with a three-dimensional pictogram, the system comprising computer-usable media storing:
   computer-readable program code for displaying a medical image;
   computer-readable program code for displaying a three-dimensional pictogram representing anatomy shown in the medical image;
   computer-readable program code for displaying a marker near but not through the three-dimensional pictogram, the marker representing a medical instrument used to create the medical image; and
   computer-readable program code for adjusting an orientation of the marker relative to the orientation of the three-dimensional pictogram in accordance with a manual adjustment received from a user via a user interface.

24. The system of claim 23, wherein the marker is manipulatable with three rotation degrees of freedom around the three-dimensional pictogram.

25. The system of claim 23 further comprising computer-readable program code for rotating the three-dimensional pictogram.

26. The method of claim 25, wherein the three-dimensional pictogram is rotatable with three degrees of freedom.

27. A system for labeling a medical image with a three-dimensional pictogram, the system comprising computer-usable media storing:
   computer-readable program code for displaying a set of three-dimensional pictograms of anatomy;
   computer-readable program code for receiving a user selection of a three-dimensional pictogram from the displayed set;
   computer-readable program code for displaying a medical image;
   computer-readable program code for displaying the selected three-dimensional pictogram near the medical image; and
   computer-readable program code for rotating the three-dimensional pictogram independent of the displayed medical image in accordance with a manual adjustment received from a user via a user interface.

28. The system of claim 27, wherein the set of three-dimensional pictograms is determined based on study type.

29. The method of claim 27, wherein the selected three-dimensional pictogram is rotatable with three degrees of freedom.

30. A system for labeling a medical image with a three-dimensional pictogram, the system comprising computer-usable media storing:
   computer-readable program code for displaying a medical image;
   computer-readable program code for displaying a three-dimensional pictogram representing anatomy shown in the medical image;
   computer-readable program code for rotating the three-dimensional pictogram to a first orientation;
   computer-readable program code for saving the medical image and three-dimensional pictogram;
   computer-readable program code for retrieving the saved medical image and three-dimensional pictogram; and
   computer-readable program code for rotating the three-dimensional pictogram, the rotation starting from the first orientation independent of the displayed medical image in accordance with a manual adjustment received from a user via a user interface.

31. The system of claim 30 further comprising computer-readable program code for creating a copy of the saved medical image and three-dimensional pictogram, wherein the three-dimensional pictogram is rotated on the copy.

32. The system of claim 30, wherein the computer-readable program code for rotating the three-dimensional pictogram from the first orientation is stored on a workstation.

33. The system of claim 30, wherein the computer-readable program code for rotating the three-dimensional pictogram from the first orientation is stored on a medical diagnostic imaging system.

34. A system for labeling a medical image with a three-dimensional pictogram, the system comprising computer-usable media storing:
   computer-readable program code for displaying a three-dimensional medical image;
   computer-readable program code for displaying a graphically-rendered three-dimensional pictogram representing anatomy shown in the three-dimensional medical image;
   computer-readable program code for receiving from a user a slicing plane through the three-dimensional medical image;
   computer-readable program code for displaying a medical image in accordance with the user-selected slicing plane; and
   computer-readable program code for displaying a portion of the three-dimensional pictogram as a wire frame instead of a graphically-rendered representation of the anatomy, the wire frame portion corresponding to a sliced-off portion of the three-dimensional medical image, wherein the remaining portion of the tree-dimensional pictogram is still displayed as a graphically rendered representation of the anatomy and not as a wire frame.

35. The system of claim 34 further comprising computer-readable program code for displaying a set of three-dimensional pictograms for user selection.

36. The system of claim 35, wherein the set of three-dimensional pictograms is determined based on study type.

* * * * *